US008449479B2

(12) United States Patent
Radzuinas et al.

(10) Patent No.: US 8,449,479 B2
(45) Date of Patent: May 28, 2013

(54) SQUEEZE ACTIVATED MEDICAL PUNCTURING DEVICE

(75) Inventors: Jeffrey Radzuinas, Wallingford, CT (US); Paul DiCesare, Easton, CT (US); Christopher A. Battles, New Haven, CT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1021 days.

(21) Appl. No.: 11/568,603

(22) PCT Filed: Apr. 29, 2005

(86) PCT No.: PCT/US2005/014968
§ 371 (c)(1),
(2), (4) Date: Mar. 17, 2009

(87) PCT Pub. No.: WO2005/107595
PCT Pub. Date: Nov. 17, 2005

(65) Prior Publication Data
US 2011/0112438 A1     May 12, 2011

Related U.S. Application Data (60) Provisional application No. 60/568,369, filed on May 5, 2004.

(51) Int. Cl.
*A61B 5/00*     (2006.01)
(52) U.S. Cl.
USPC .......................................... 600/583

(58) Field of Classification Search
USPC ............................ 600/573, 583; 606/181, 182
See application file for complete search history.

(56) References Cited

U.S. PATENT DOCUMENTS

| | | | |
|---|---|---|---|
| 3,760,809 A | 9/1973 | Campbell | |
| 4,817,603 A | 4/1989 | Turner et al. | |
| 4,869,249 A | 9/1989 | Crossman et al. | |
| 4,900,311 A | 2/1990 | Stern et al. | |
| 5,487,748 A * | 1/1996 | Marshall et al. | 606/182 |
| 5,540,709 A | 7/1996 | Ramel | |
| 5,755,733 A | 5/1998 | Morita | |
| 6,136,013 A | 10/2000 | Marshall et al. | |
| 6,168,606 B1 * | 1/2001 | Levin et al. | 606/181 |

(Continued)

FOREIGN PATENT DOCUMENTS

| | | |
|---|---|---|
| EP | 0293092 A2 * | 11/1988 |
| EP | 1219242 | 7/2002 |

(Continued)

*Primary Examiner* — Max Hindenburg
(74) *Attorney, Agent, or Firm* — The Webb Law Firm (57) ABSTRACT

The medical puncturing device (10) includes a housing (12) having a proximal end (18) and a distal end (16) and a skin puncturing assembly (14) within the housing. The skin puncturing assembly includes a movable carrier (50) and a skin puncturing element (52). The skin puncturing element is adapted to puncture the skin of a patient. The carrier is movable from a retracted position wherein a distal tip of the skin puncturing element is disposed within the housing, to a puncturing position wherein the distal tip is exposed to puncture the skin of the patient. The carrier is moved from the retracted position to the puncturing position upon radial deformation of the housing. An internal guide (42) may be provided within the housing for guiding the movement of the carrier from the retracted position to the puncturing position.

25 Claims, 9 Drawing Sheets

U.S. PATENT DOCUMENTS

| | | |
|---|---|---|
| 6,248,120 B1 | 6/2001 | Wyszogrodski |
| 6,432,120 B1 | 8/2002 | Teo |
| 6,626,868 B1 | 9/2003 | Prestidge et al. |
| 6,719,771 B1 | 4/2004 | Crossman |
| 7,235,056 B2 * | 6/2007 | Duchon et al. ............... 600/583 |
| 2001/0039387 A1 * | 11/2001 | Rutynowski et al. ......... 600/573 |
| 2002/0169470 A1 * | 11/2002 | Kuhr et al. .................... 606/182 |

FOREIGN PATENT DOCUMENTS

| | | |
|---|---|---|
| EP | 1219242 A1 * | 7/2002 |
| JP | 2001095787 A | 4/2001 |
| JP | 2002526174 A | 8/2002 |
| WO | 0020058 A1 | 4/2000 |

* cited by examiner

SQUEEZE ACTIVATED MEDICAL PUNCTURING DEVICE

CROSS-REFERENCE TO RELATED APPLICATIONS

This application claims the benefit of U.S. Provisional Application No. 60/568,369, filed May 5, 2004.

BACKGROUND OF THE INVENTION

1. Field of the Invention

The present invention relates generally to medical puncturing devices, commonly referred to as lancets, used to take blood samples from patients and, more specifically, to a medical puncturing device that ensures sterility before use, and safe and secure disposal after use.

2. Description of Related Art

Medical puncturing devices are used in the medical field for puncturing the skin of a patient to obtain a capillary blood sample from the patient. Certain diseases, such as diabetes, require that the patient's blood be tested on a regular basis to monitor, for example, the patient's blood sugar levels. Additionally, test kits, such as cholesterol test kits, often require a blood sample for analysis. The blood collection procedure usually involves pricking a finger or other suitable body part in order to obtain the blood sample. Typically, the amount of blood needed for such tests is relatively small and a small puncture wound or incision normally provides a sufficient amount of blood for these tests.

Various medical puncturing devices are commercially available to hospitals, clinics, doctors' offices, and the like, as well as to individual consumers. Such devices typically include a sharp-pointed member such as a needle, or a sharp-edged member such as blade, that is used to make a quick puncture wound or incision in the patient's skin in order to provide a small outflow of blood. It is often physiologically and psychologically difficult for many people to prick their own finger with a hand-held needle or blade. As a result, medical puncturing devices have evolved into automatic devices that puncture or cut the skin of the patient upon the actuation of a triggering mechanism. In some devices, the needle or blade is kept in a standby position until it is triggered by the user, who may be a medical professional in charge of drawing blood from the patient, or the patient himself or herself. Upon triggering, the needle or blade punctures or cuts the skin of the patient, for example on the finger. Often, a spring is incorporated into the device to provide the "automatic" force necessary to puncture or cut the skin of the patient.

It is important in the medical field that such medical puncturing devices or lancets be in a sterile condition before use. Today, medical puncturing devices or lancets are manufactured and packaged in a sterilized condition before they are distributed to medical professionals and members of the public who have a need for such devices. The sterile packaging maintains the sterility of the device, ensuring that the surrounding environment does not contaminate it until use. In addition, it is also of increasing importance that the user or another person does not come into contact with the needle or blade after use of the device. With the concern over blood-borne diseases, medical professionals are required to take great care with medical devices that come into contact with the blood of patients. Thus, an important aspect of medical puncturing device/lancet design is concerned with preventing the needle or blade of the device from wounding the user or another person after the blood sample is drawn from the patient. Once used, the needle or blade should be shielded to prevent the needle or blade from wounding the user or another person handling the device. Moreover, the medical puncturing device or lancet should be disposable to eliminate the chances of disease transmission due to the needle or blade being used on more than one person. In this regard, the medical puncturing device or lancet should ideally be designed for one firing, and have safety features to prevent reuse.

Advances have been made in recent years to increase safety in operating and handling used medical puncturing devices. For example, medical puncturing devices are currently available which are single shot devices that feature automatic ejection and retraction of the puncturing or cutting element from and into the device. Examples of such medical puncturing devices are disclosed in U.S. Pat. Nos. 6,432,120; 6,248,120; 5,755,733; and 5,540,709.

U.S. Pat. No. 6,432,120 to Teo discloses a lancet assembly that includes a lancet holder, which contains a spring-loaded lancet structure. The spring-loaded lancet structure includes a single spring that effects the ejection and retraction of a lancet needle upon the triggering of the structure. U.S. Pat. No. 6,248,120 to Wyszogrodzki discloses a puncturing device comprised of a housing, shielding portion, a piston with a puncturing tip, and drive and return springs that eject and retract the piston, respectively, upon the breakage of internal wing elements in the housing. U.S. Pat. No. 5,755,733 to Morita discloses a lancet assembly that includes a combined holder and lancet structure. The lancet structure includes a lancet member with a puncturing tip and a compressible spring member that causes the lancet member to puncture the skin of a patient upon actuation of a pair of actuating arms.

U.S. Pat. No. 5,540,709 to Ramel discloses a lancet device that includes a housing enclosing a slidable trigger, which is used to trigger a compressed spring that powers a piercing lancet member to pierce the skin of a patient. The housing includes a pair of internal fingers that engage the body of the lancet member, which are then released of engagement with the lancet member body by axial force applied by the user to the slidable trigger. Other medical puncturing devices or lancets known in the art are disclosed in U.S. Pat. Nos. 4,869,249 and 4,817,603. The devices disclosed in these references include a cap that is used to protect the needle or to keep the needle sterile.

U.S. Pat. Nos. 6,136,013 to Marshall et al. and 6,719,771 to Crossman disclose a lancet device that includes a housing with a trigger integral with the housing in the form of a tongue provided by a U-shaped cut in the housing. The tongue is deformable inwardly and when depressed, passes through an aperture (e.g. cut-out, gap, or opening) in the housing and causes release or disengagement of a piercing lancet member to pierce the skin of a patient.

Other medical puncturing devices or lancets known in the art are disclosed in U.S. Pat. Nos. 4,869,249 and 4,817,603. The devices disclosed in these references include a cap that is used to protect the needle or to keep the needle sterile.

SUMMARY OF THE INVENTION

In view of the foregoing, a need generally exists in the medical field for an improved medical puncturing device that ensures sterility before use, and safe and secure disposal after use. Additionally, a need exists in the medical field for a simple, inexpensive, reliable, self-activating, and disposable medical puncturing device for use in collecting blood samples. Moreover, there is a need for a medical puncturing device in which production of puncture wounds and/or incisions is consistent and well-controlled.

The foregoing needs are fulfilled with a medical puncturing device in accordance with the present invention. The medical puncturing device generally includes a deformable housing and a skin puncturing element disposed within the housing, wherein, upon radial deformation of the housing, the skin puncturing element is movable from a first position wherein a tip of the skin puncturing element is disposed within the housing to a second position causing the tip to be exposed.

In accordance with another embodiment of the invention, a medical puncturing device is provided comprising a deformable housing, wherein at least a portion of the deformable housing includes a continuous cross-section, wherein a portion of the continuous cross-section includes at least one point of deformation, and a skin puncturing element disposed within the housing. Upon deformation of the housing at the at least one point, the skin puncturing element is movable from a first position wherein a tip of the skin puncturing element is disposed within the housing to a second position causing the tip to be exposed.

In yet another embodiment of the invention, a medical puncturing device is provided comprising a deformable housing having a proximal end and a distal end, and a skin puncturing assembly disposed within the housing. The skin puncturing device comprises a movable carrier and a skin puncturing element mounted to the carrier. The skin puncturing element comprises a distal tip for puncturing the skin of a patient The carrier is movable from a retracted position wherein the sharp distal tip is disposed within the housing to a puncturing position wherein the distal tip is exposed to puncture the skin of the patient. One of the housing and carrier includes at least one detent in interference engagement within the at least one engagement formed in the other of the housing and carrier for securing the carrier in the retracted position. Radial deformation of the housing causes the at least one detent to move out of interference engagement with the at least one engagement, such that the carrier is moved from the retracted position to the puncturing position.

DETAILED DESCRIPTION OF THE INVENTION

For purposes of the description hereinafter, the terms "upper", "lower", "right", "left", "vertical", "horizontal", "top", "bottom", and derivatives thereof shall relate to the invention as it is oriented in the drawing figures. However, it is to be understood that the invention may assume many alternative variations and step sequences except where expressly specified to the contrary. It is also to be understood that the specific devices and processes illustrated in the attached drawings and described in the following text are simply exemplary embodiments of the invention. Hence, specific dimensions and other physical characteristics related to the embodiments disclosed hereinafter are not to be considered limiting.

Figure 2:
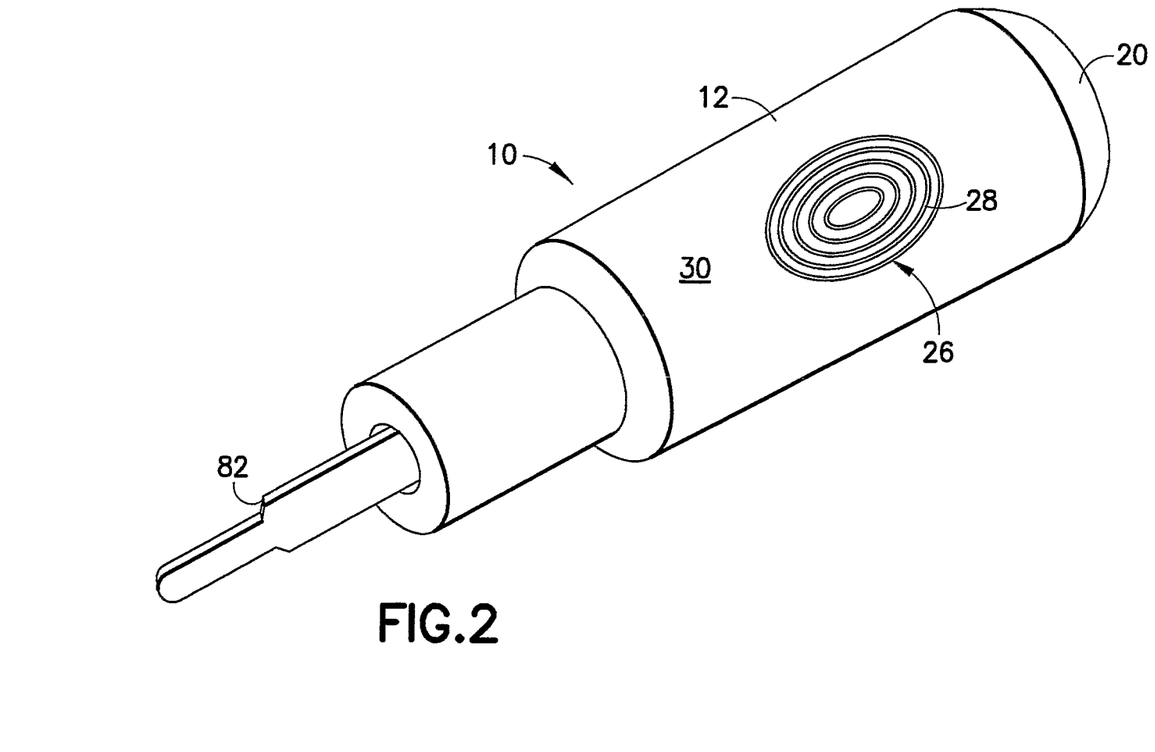
FIG. 2 is a perspective view of the medical puncturing device shown in FIG. 1 viewed from an opposite side of the device.
Figure 3:
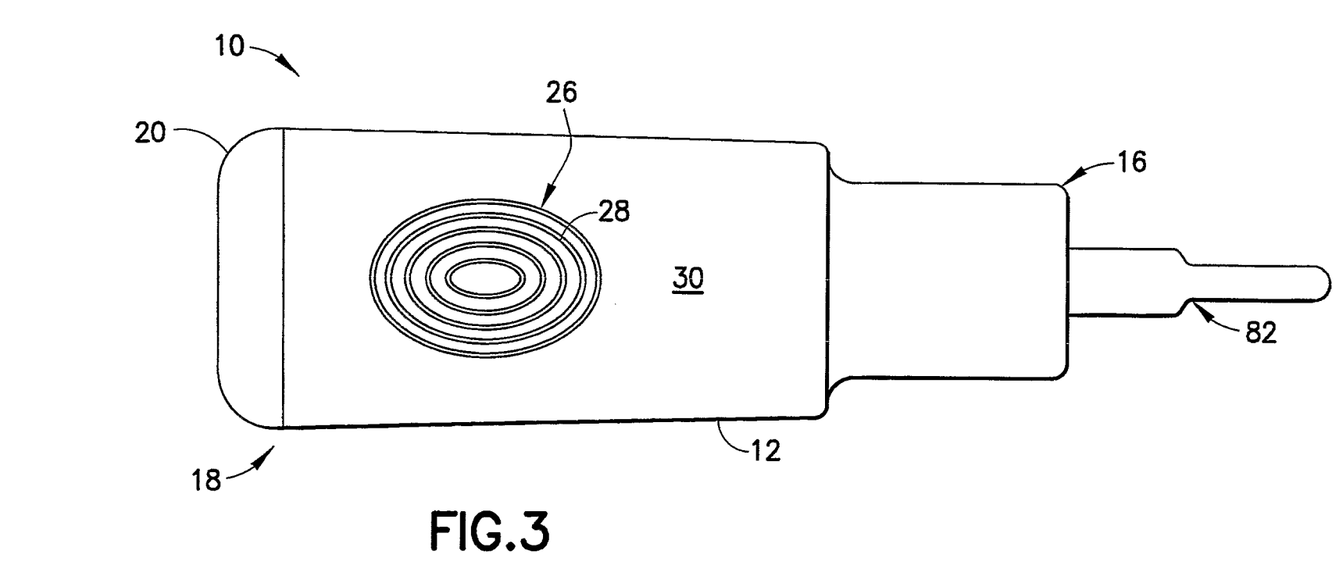
FIG. 3 is an elevational view of the medical puncturing device shown in FIGS. 1 and 2.
Figure 4:
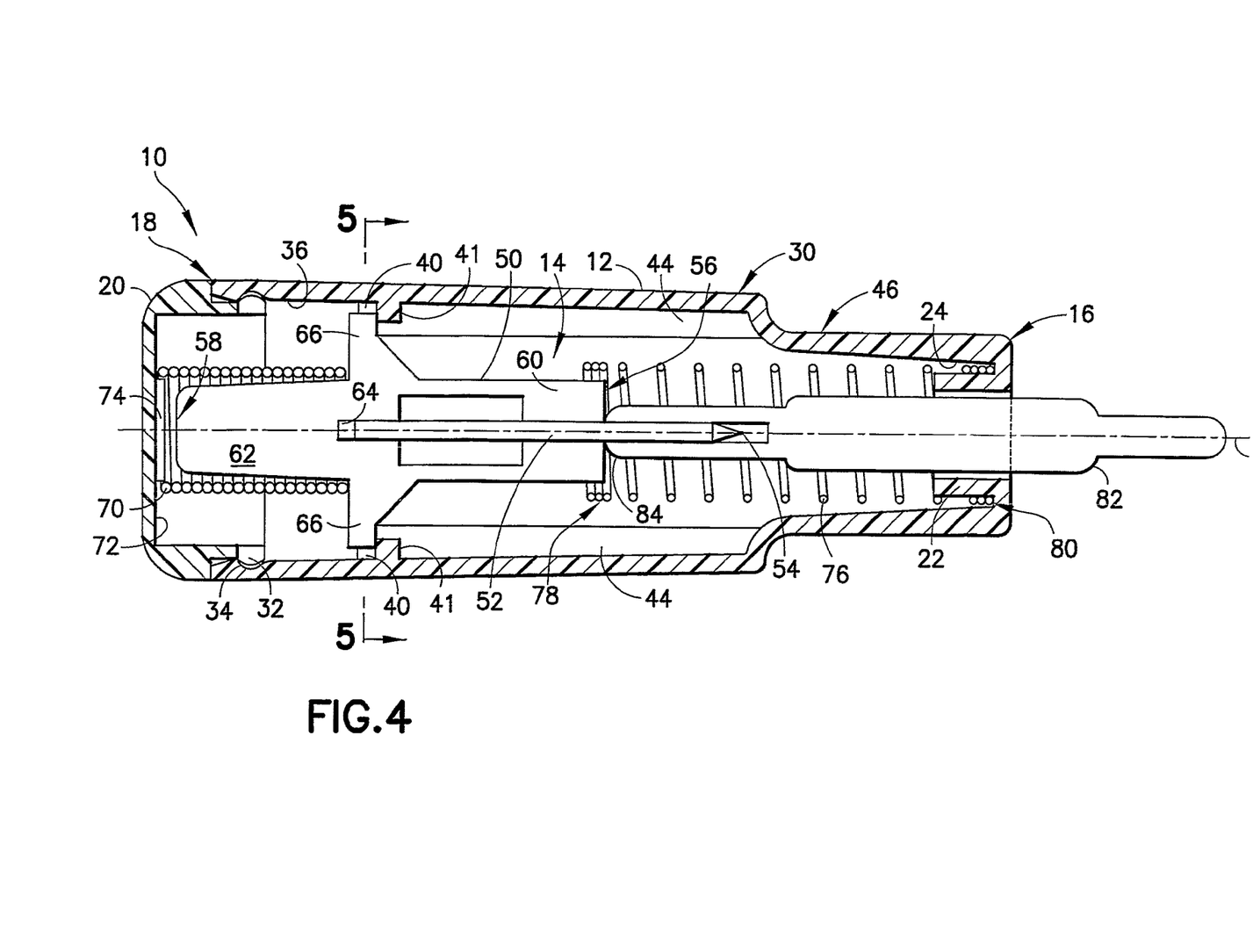
FIG. 4 is a longitudinal cross-sectional view of the medical puncturing device shown in FIGS. 1 and 2.

Referring to FIGS. 1-5, a medical puncturing device or lancet 10 (hereinafter "puncturing device 10") in accordance with the present invention is generally illustrated. The puncturing device 10 generally includes a housing 12 and a skin puncturing assembly 14 disposed within the housing 12. The housing 12 is preferably a generally tubular structure having a distal end 16 and a proximal end 18. The housing 12 is preferably open-ended at the distal and proximal ends 16, 18. An end cap 20 may be provided at the proximal end 16 of the housing 12 to close the proximal end 18 of the housing 12. Alternatively, the housing 12 may be formed to have a closed proximal end 18 instead of the end cap 20 illustrated in FIG. 4. The closed proximal end 18 of the housing 12 would be integrally formed with the remainder of the body of the housing 12 in this variation of the puncturing device 10. As shown in FIG. 4, the housing distal end 16 may be formed with an internally-extending portion 22. The internally-extending portion 22 defines a recess or pocket 24 for housing a spring or other biasing element as discussed further herein.

Figure 1:
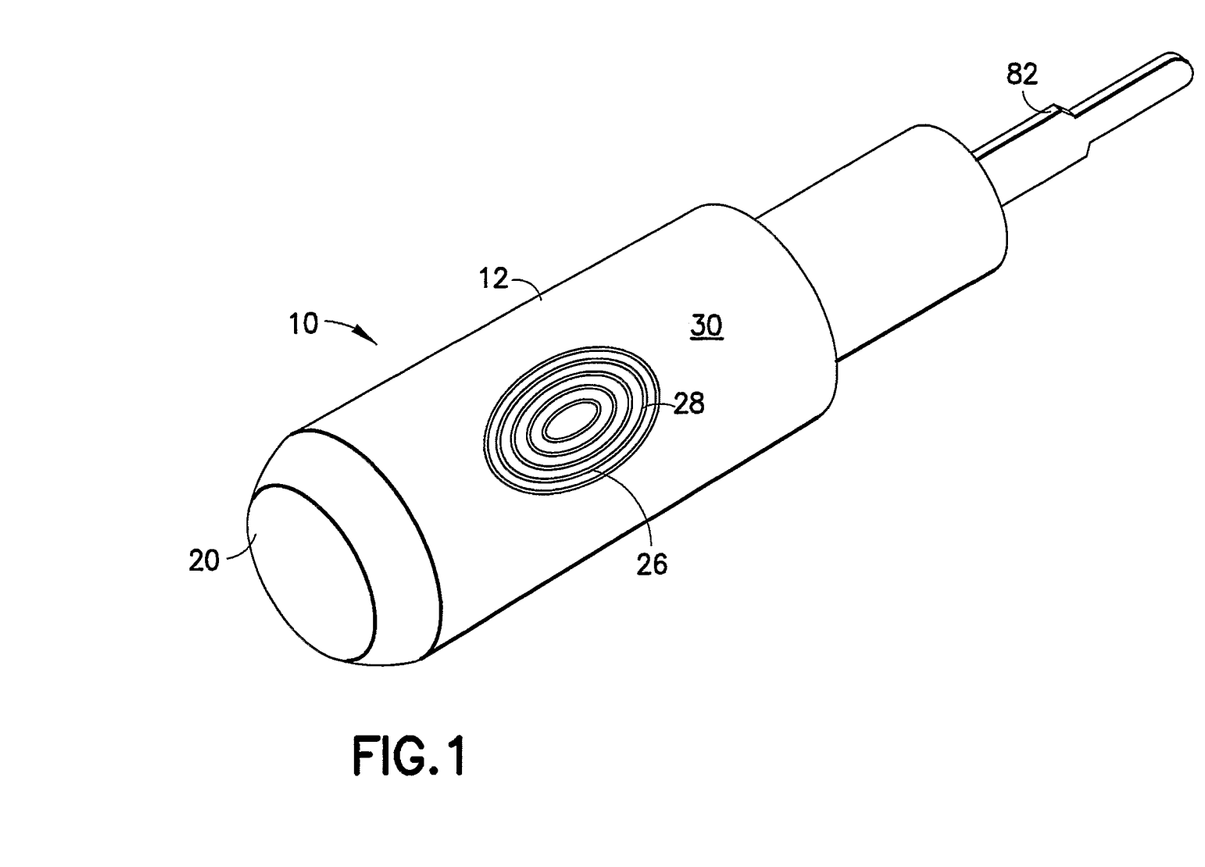
FIG. 1 is a perspective view of a medical puncturing device in accordance with the present invention, showing the device with a removable tip guard.

Preferably, the housing 12 is made of a resiliently deformable material, such as suitable medical grade plastic, which allows the housing to be deformed radially toward a central axis L of the housing 12, to actuate the puncturing device 10 as discussed herein. The end cap 20 may also be made of a similar material to the housing 12. The housing 12 may have any suitable cross-sectional shape, such as oval, circular, or polygonal. However, because the housing 12 is intended to be grasped between the fingertips of the user of the puncturing device 10, the cross-sectional shape of the housing 12 is preferably selected so that the housing 12 is easily manipulated by the user's fingertips. An oval or circular cross-sectional shape for the housing 12 best fits this requirement and is presently preferred. Additionally, the housing 12 is formed with finger pads 26 provided on opposing sides of the housing 12 for grasping by the user of the puncturing device 10. The finger pads 26 illustrated in FIGS. 1-3 are formed as concentric oval rings 28 and are raised from an outer or external surface 30 of the housing 12 to provide gripping surfaces for the user of the puncturing device 10. The finger pads 26 provide a tactile indication of where the user of the puncturing device 10 should place his or her fingertips to actuate the puncturing device 10 in the manner described in detail herein.

The end cap 20, if present, is engaged with the housing 12 by a frictional, snap-fit type of engagement. Once engaged with the housing 12, the frictional engagement between the end cap 20 and housing 12 is of sufficient strength to substantially prevent the end cap 20 from being removed easily from the housing 12 to reduce the ability of a user of the puncturing device 10 to tamper with the puncturing device 10 after manufacturing. In particular, the end cap 20 includes a circumferential detent 32 that cooperates with a circumferential recess 34 formed in an internal surface 36 of the housing 12. To further secure the connection between the end cap 20 and housing 12, a medical-type adhesive may be provided in the recess 34 during the assembling process for the puncturing device 10, thereby adhesively securing the detent 32 in the recess 34.

The housing 12 is further formed with opposing internal pockets 40 formed by opposing internally-extending portions 41 of the housing 12. The internal pockets 40 are adapted to restrain the movement of the skin puncturing assembly 14 within the housing 12, as discussed herein. Additionally, the housing 12 is formed with internal guides 42 for guiding the movement of the skin puncturing assembly 14 within the housing 12, once the skin puncturing assembly 14 is released of engagement with the internal pockets 40. The guides 42 are preferably in the form of internal guide tracks 44. The guide tracks 44 may be formed integrally with the housing 12, and generally extend along the internal surface 36 of the housing 12. The guide tracks 44 generally extend from an area proximate to the end cap 20 to a distal portion 46 of the housing 12, where the diameter of the housing 12 is reduced or necked inward. The distal portion 46 of the housing 12 generally encompasses or surrounds the internally-extending portion 22 of the housing 12 discussed previously. The internal pockets 40 and guides 42 are formed in the housing 12 along respective transverse axes $S_1$, $S_2$, which are oriented approximately perpendicular to each other (i.e., about 90° apart) for proper operation of the puncturing device 10, as discussed herein. The fingerpads 26 are formed generally along axis $S_2$ to ensure proper operation of the puncturing device 10, as discussed herein, but may be formed along axis $S_1$ in an alternative embodiment of the puncturing device 10 shown in FIGS. 11 and 12.

Figures 5, 7, 10:
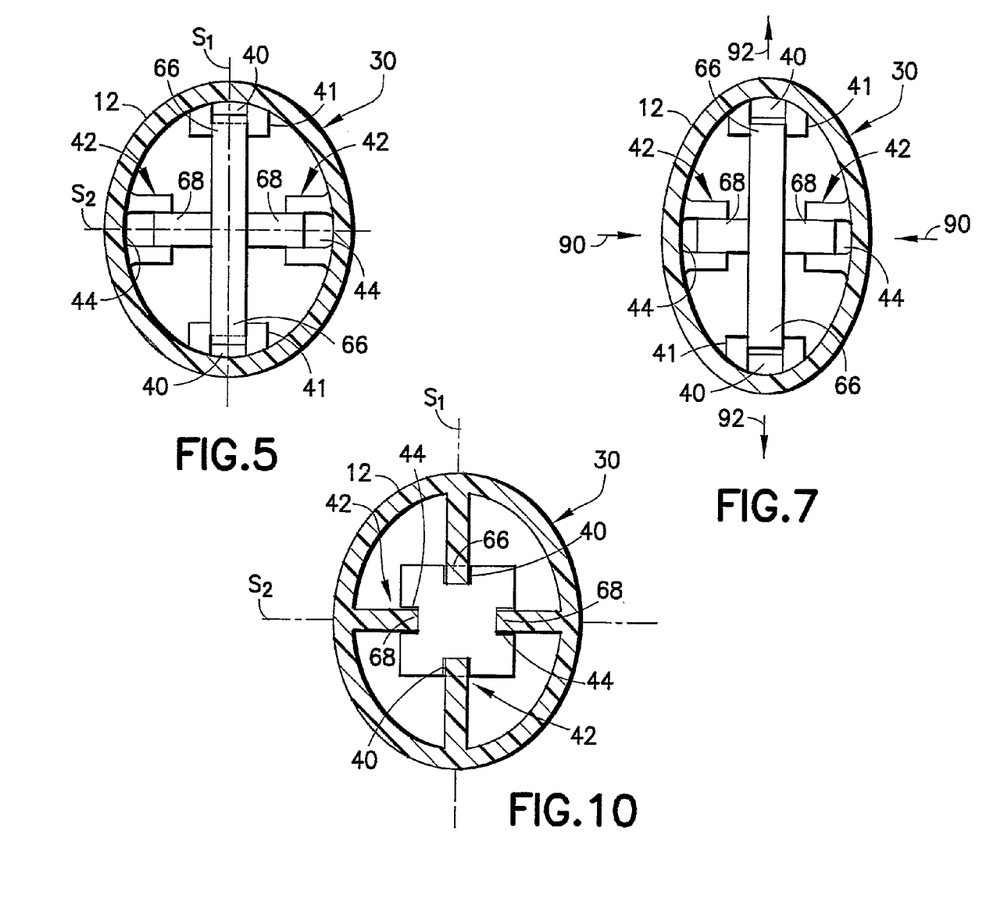
FIG. 5 is a cross-sectional view taken along line 5-5 in FIG. 4.
FIG. 7 is a cross-sectional view taken along line 7-7 in FIG. 6, showing the direction of forces applied to actuate the device.
FIG. 10 is a cross-sectional view of an alternative configuration of the medical puncturing device of the present invention.

As shown in the FIG. 5 (as well as FIGS. 7, 10 and 12), a cross-section view cut through the housing at the location point wherein radial deformation causes release of interfering engagement is continuous in nature, such that cuts or gaps in the housing are not necessary for causing release of the interfering engagement holding the carrier in the retracted position. Having cuts or gaps in the housing can be disadvantageous and may add to the molding complexity of puncture devices. By providing a housing that is continuous in nature at a radial deformation point allows for simplified molding of housing components for puncturing devices. Additionally, since gaps or cuts in the housing are not needed or may be reduced, blood that remains on the sharp distal tip after use is further protected from leaking out of the housing through gaps or cuts that sometimes exist in the lancet housing.

The skin puncturing assembly 14 is disposed within the housing 12 as illustrated in FIG. 4. The skin puncturing assembly 14 is generally comprised of an elongated carrier member 50 (hereinafter "carrier 50") and a skin puncturing element 52. The skin puncturing element 52 may be a needle, blade, or like puncturing or cutting element, and includes a sharp distal tip 54 for puncturing or cutting the skin of a patient from which a blood sample is to be taken. The carrier 50 is movably mounted in the housing 12 as discussed herein. The carrier 50 preferably has a generally cylindrical shape to fit within the preferred oval or circular-shaped cross-sectional shape of the housing 12. However, other cross-sectional shapes for the carrier 50, such as polygonal, are also within the scope of the present invention.

The carrier 50 includes a first or distal end 56 and a second or proximal end 58. The distal end 56 faces the distal end 16 of the housing 12. Likewise, the proximal end 58 of the carrier 50 faces the proximal end 18 of the housing 12 and the end cap 20. The body of the carrier 50 is formed with a substantially cylindrical-shaped distal portion 60 and a substantially cylindrical-shaped proximal portion 62 extending from the distal and proximal ends 56, 58 of the carrier 50, respectively. The skin puncturing element 52 generally extends from the distal end 56 of the carrier 50 and is received within a central bore 64 formed within the distal portion 60 of the carrier 50. The skin puncturing element 52 may be secured in the central bore 64 by a medical grade adhesive or by other means customary in the medical field. The skin puncturing element 52 is depicted in the Figures of this disclosure as a needle. However, as indicated previously, the skin puncturing element 52 is not necessarily limited to a needle or other puncturing-type element, but could also be a blade for causing an incision-type wound in the skin of a patient when the puncturing device 10 is activated.

Figure 8:
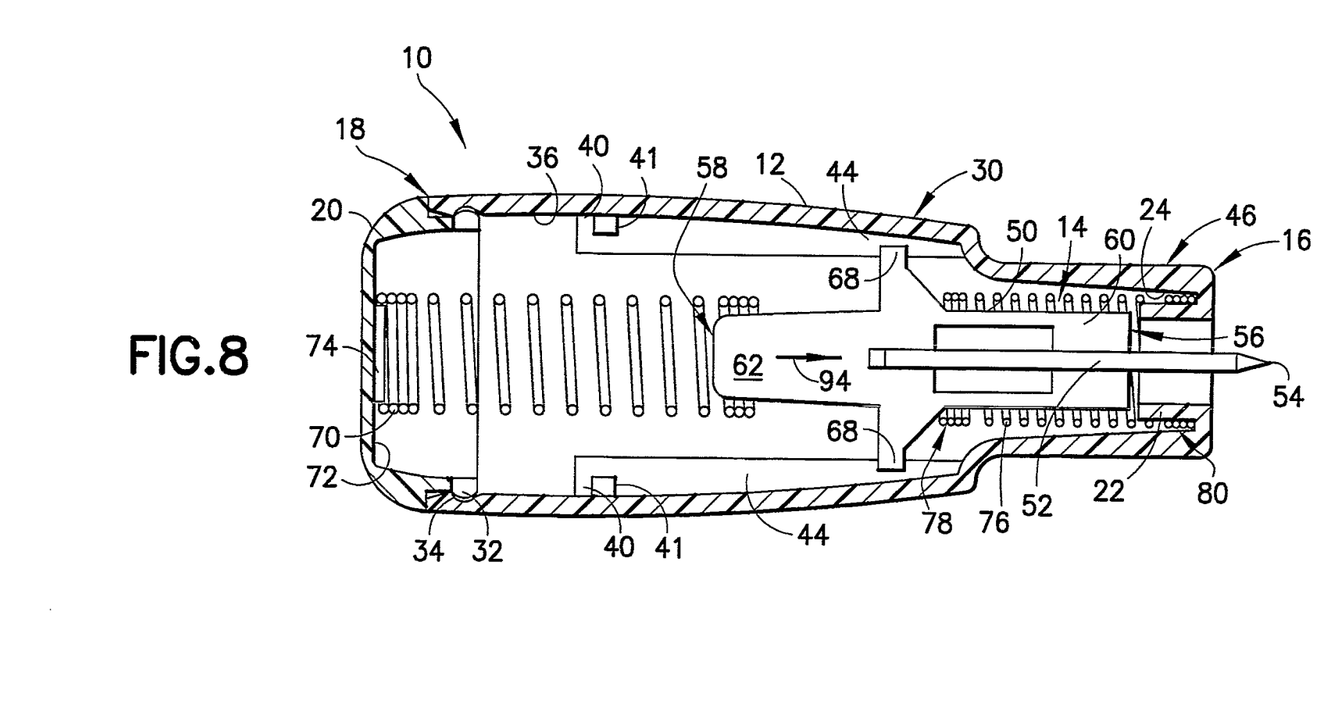
FIG. 8 is a cross-sectional view of the medical puncturing device shown in FIGS. 1 and 2, showing the device immediately after actuation with a skin piercing element of the device exposed momentarily to pierce the skin of a patient.

The carrier 50 is further preferably formed with two opposing pairs of detents 66, 68 that are used to secure the carrier 50 in a pre-actuated state in the housing 12 and guide the movement of the carrier 50 in housing 12 when the puncturing device 10 is actuated by a user. First pair of detents 66 engages or cooperates with the internal pockets 40 in the housing 12 to secure the carrier 50 in the pre-actuated or "retracted" position, as shown in FIG. 4. The second pair of detents or guide elements 68 engages or cooperates with the internal guides 42 and, more particularly, the guide tracks 44 in the housing 12 to guide the movement of the carrier 50 from the retracted position as shown in FIG. 4 to an extended or puncturing position, which is illustrated in FIG. 8 discussed herein. As shown in FIG. 5, the carrier 50 is formed such that the two pairs of opposing detents 66, 68 form a crosshair-type configuration with the housing 12, and extend along orthogonal axes $S_1$, $S_2$, respectively.

The guides 42 (i.e., guide tracks 44) and detents or guide elements 68 cooperating therewith are entirely optional in the puncturing device 10, but this arrangement is preferred because it improves the reliability and performance of the puncturing device 10 by guiding the movement of the carrier 50 within the housing 12. Additionally, while embodiments of the present invention are described herein with reference to two opposing pairs of detents 66, 68, it will be appreciated that only one detent 66 engaging or co-acting with one internal pocket 40 is necessary to inhibit movement of the carrier 50 relative to the housing 12 for proper functioning of the puncturing device 10. Similarly, the second pair of detents or guide elements 68 may be reduced to a single detent or guide element 68 engaging or co-acting with a single guide 42 (i.e., guide track 44) in accordance with the present invention.

It will be appreciated that the locations of the detents 66 and internal pockets 40 may be reversed in accordance with an embodiment of the present invention, as generally illustrated in FIG. 10. Thus, the detents 66 could be made to extend from the internal surface or wall 36 of the housing 12 and cooperate with internal pockets 40 formed in the body of the carrier 50. Likewise, the locations for the guide elements 68 and guides 42 (i.e., guide tracks 44) may be reversed in accordance with the present invention. The guide elements 68 could be made to extend from the internal surface or wall 36 of the housing 12 and cooperate with guide tracks 44 formed in the body of the carrier 50. Such reversals of locations are within the skill of those skilled in the art.

Referring again to FIGS. 1-5, the puncturing device 10 further includes a drive or firing spring 70 disposed in the housing 12 which, when activated, moves the puncturing assembly 14 within the housing 12, and provides the force necessary to puncture the skin of a patient when the puncturing device 10 is used in a blood-drawing or collecting procedure. More particularly, the drive spring 70 is adapted to move the carrier 50 within the housing 12 from the retracted position shown in FIG. 4 to the extended or puncturing position, shown in FIG. 8 discussed herein, wherein the skin puncturing element 52 extends outward from the distal end 16 of the housing 12, and the sharp distal tip 54 of the skin puncturing element 52 is exposed for causing a puncturing or incision-type wound in the skin of the patient.

The drive spring 70 is generally received at least partially about the proximal portion 62 of the carrier 50 and extends between the proximal portion 62 of the carrier 50 and an inner surface or side 72 of the end cap 20. The inner side 72 of the end cap 20 may include a centering protrusion 74 to maintain the positioning of the drive spring 70 prior to actuation of the puncturing device 10. As shown in FIG. 4, the drive spring 70 is preferably held in a compressed state within the housing 12 prior to actuation of the puncturing device 10 by interference engagement between the detents 66 on the carrier 50 and the internal pockets 40 in the housing 12. The proximal portion 62 of the carrier 50 is preferably tapered toward the central axis L, such that drive spring 70 is held securely on the proximal portion 62 by a frictional engagement therewith to maintain the drive spring 70 in the compressed state. A medical adhesive or a simple mechanical fastener may further be used to secure the drive spring 70 to the proximal portion 62. The crosshair configuration of the detents 66, 68 shown in FIG. 5 may further help maintain the drive spring 70 in the compressed state.

The puncturing device 10 optionally further includes a return or retraction spring 76 disposed in the housing 12 to provide the force necessary to generally return the skin puncturing assembly 14 to a static condition within the housing 12 after the puncturing device 10 is actuated by a user. More particularly, the retraction spring 76 provides the force necessary to return the carrier 50 to a position within the housing 12 wherein the skin puncturing element 52 and the sharp distal tip 54 thereof are fully contained within the housing 12. Generally, during actuation of the puncturing device 10, the drive spring 70 moves the carrier 50 from the retracted position (FIG. 4) wherein the sharp distal tip 54 of the puncturing element 52 is disposed within the housing 12 to the exposed or puncturing position (FIG. 8) wherein the sharp distal tip 54 emerges from the distal end 16 of the housing 12 for causing a puncturing or incision-type wound in the skin of a patient. The retraction spring 76 is generally used to return the carrier 50 to a position within the housing 12 wherein the skin puncturing element 52 is fully contained within the housing 12.

The retraction spring 76 is generally received about the distal portion 60 of the carrier 50 and extends between the distal portion 60 and the distal end 16 of the housing 12. In particular, a proximal end 78 of the retraction spring 76 is connected to the distal portion 60 of the carrier 50 and a distal end 80 of the retraction spring 76 is preferably seated in the pocket 24 formed by the internally-extending portion 22 of the housing 12. The retraction spring 76 generally acts between the distal portion 60 of the carrier 50 and the distal end 16 of the housing 12. The retraction spring 76 is in a generally uncompressed state prior to actuation of the puncturing device 10 as shown in FIG. 4. The proximal and distal ends 78, 80 of the retraction spring 76 may be secured to the distal portion 60 of the carrier 50 and in the pocket 24, respectively, by a suitable medical grade adhesive, if desired. Otherwise, a simple frictional engagement between the proximal and distal ends 78, 80 and the distal portion 60 of the carrier 50 and the pocket 24, respectively, is all that is necessary to secure the retraction spring 76 to the carrier 50 and housing 12 in accordance with the present invention.

The skin puncturing assembly 14 may further include a protective tip guard 82 connected to the carrier 50. The tip guard 82 may be formed integrally with the body of the carrier 50, but includes a notched connection 84 with the distal end 56 of the carrier 50. The notched connection 84 is entirely optional and the skin puncturing element 82 may be received in a central bore in the tip guard 82, and be maintained therein by frictional engagement with the central bore in the tip guard 82. The tip guard 82 extends outward from the distal end 16 of the housing 12 as shown in FIGS. 1-4. The notched connection 84 enables the user of the puncturing device 10 to break the integral connection between the tip guard 82 and carrier 50, and remove the tip guard 82 prior to actuating the puncturing device 10. The tip guard 82 ensures that the sharp distal tip 54 of the puncturing element 52 remains sterile before use and, further, protects the user against accidental puncture wounds that could be caused by inadvertent or premature actuation of the puncturing device 10. The tip guard 82 may be removed by simply pulling on the tip guard 82 and/or moving the tip guard 82 in a side-to-side manner in the open distal end 16 of the housing 12 until the notched connection 84 with the carrier 50 breaks, as is well-known in the art.

The assembly of the puncturing device 10 is a simple and straight forward process. The housing 12 is first provided and, as discussed previously, includes the open distal and proximal ends 16, 18. Next, the retraction spring 76 may be inserted into the open proximal end 16 of the housing 12, such that the distal end 80 of the retraction spring 76 is received in the pocket 24 formed at the distal end 16 of the housing 12. Once the retraction spring 76 is in place, the skin puncturing assembly 14 may be inserted into the open proximal end 18 of the housing 12. The skin puncturing assembly 14 is generally inserted into the housing 12 so that the detents 66, 68 engage the internal pockets 40 and guides 42 (i.e., guide tracks 44), respectively. The retraction spring 76 may be pre-assembled to the carrier 50, so that the retraction spring 76 is placed in position in the housing 12 during the same insertion step as the skin puncturing assembly 14. The internal pockets 40 and guides 42 ensure the skin puncturing assembly 14 is properly loaded into the housing.

Figure 6:
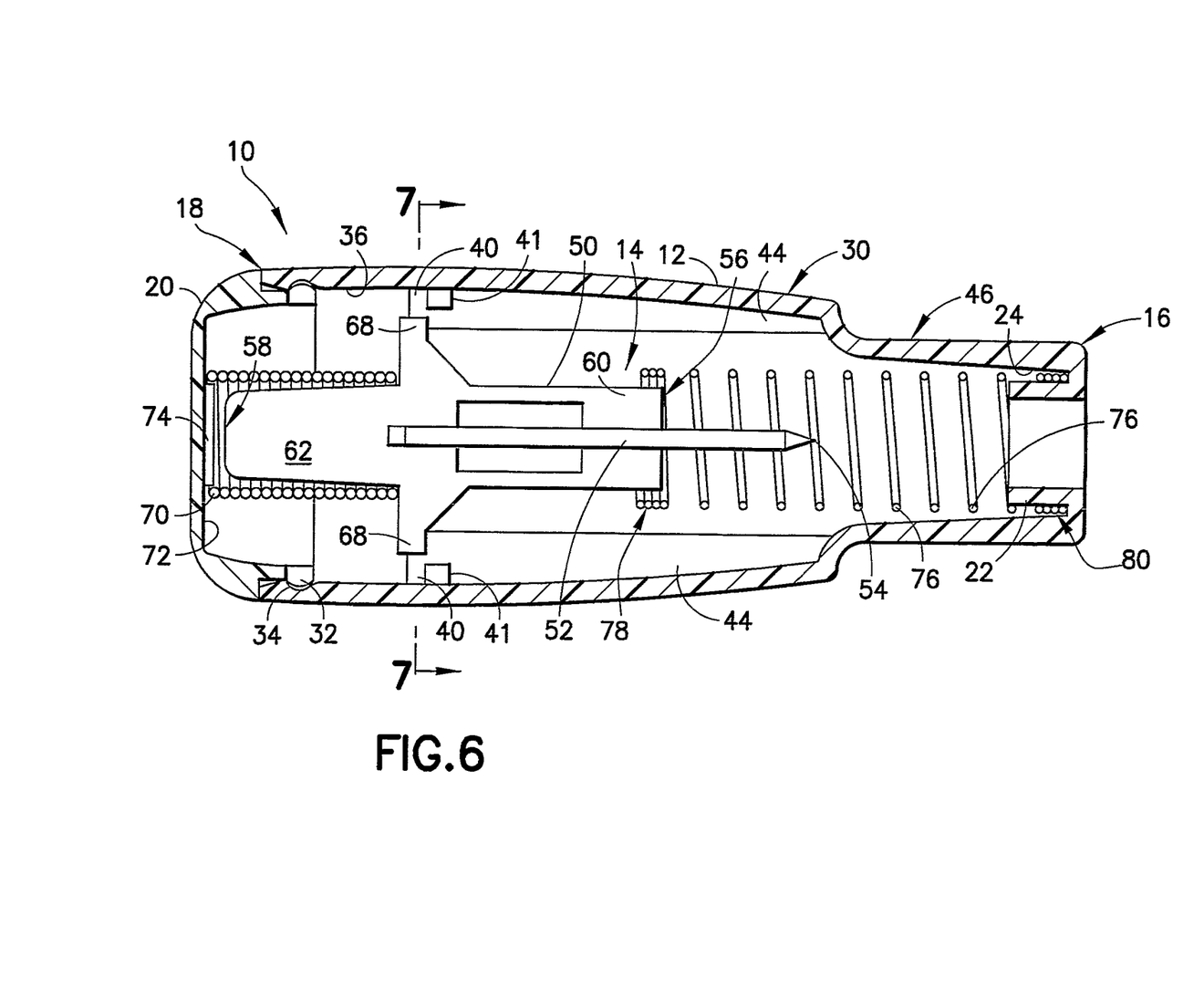
FIG. 6 is a cross-sectional view of the medical puncturing device shown in FIGS. 1 and 2 prior to actuation of the device and with the tip guard removed.

With the retraction spring 76 and skin puncturing assembly 14 in place within the housing 12, the drive spring 70 may be inserted into the housing 12 through the open proximal end 18 of the housing 12. The drive spring 70 is received about the proximal portion 62 of the carrier 50 and extends from the proximal portion 62 towards the open proximal end 18 of the housing 12. The housing proximal end 18 is then closed with the end cap 20. The drive spring 70 is generally placed in a compressed, pre-actuated state within the housing 12 by affixing the end cap 20 to the housing proximal end 18. The assembled puncturing device 10 is now ready for use. Referring to FIGS. 5-9, the sequence of actuation for the puncturing device 10 will now be discussed. FIG. 6 shows the puncturing device 10 in a pre-actuated state in a similar manner to FIG. 4 discussed previously, but with the tip guard 82 removed. In the pre-actuated state, the detents 66 of the carrier 50 are in interference engagement with the internal pockets 40 in the housing 12. The engagement of the detents 66 in the pockets 40 maintains the drive spring 70 in a compressed state between the end cap 20 and the proximal portion 62 of the carrier. Additionally, in the pre-actuated state, the retraction spring 76 extends between the distal portion 60 of the carrier 50 and the pocket 24 formed at the distal end 16 of the housing 12, but does not exert substantial force between these elements until the puncturing device 10 is actuated.

To actuate the puncturing device 10, the user grasps the housing 12 between the thumb and forefinger, preferably with the thumb and forefinger substantially engaging the fingerpads 26 on the external surface 30 of the housing 12. The user then placed the distal end 16 of the housing 12 in contact with the body part where a blood sample is to be taken. The fingerpads 26 are generally oriented along axis $S_2$, which passes through the guides 42. Thus, the fingerpads 26 generally coincide with the guides 42 as shown in FIG. 7. The user then exerts inward or radial force, as represented by arrows 90 in FIG. 7, on the housing 12 by squeezing the fingerpads 26 together. This simultaneously causes the housing 12 to deform or expand along axis $S_1$, as represented by arrows 92 in FIG. 7. As the housing 12 deforms or expands along axis $S_1$, the detents 66 engaging the internal pockets 40 are released from interference engagement with the internal pockets 40, thereby allowing the carrier 50 to move within the housing 12.

Once the interference engagement between the detents 66 and internal pockets 40 is released, the compressed drive spring 70 is also released. The drive spring 70 automatically biases or drives the carrier 50 toward the distal end 16 of the housing 12. The guides 42 (i.e., guide tracks 44) in the housing 12 guide the movement of the carrier 50 in the housing 12 toward the distal end 16 of the housing 12.

FIG. 8 shows the released movement of the carrier 50 in the housing 12. The carrier 50 is released from the retracted position or configuration shown in FIG. 6 and moves to the puncturing position or configuration shown in FIG. 8, wherein the puncturing element 52 extends from the distal end 16 of the housing 12 and the sharp distal tip 54 of the puncturing element 52 is fully exposed for piercing or cutting the skin of a patient. The carrier 50 is released by a simple act of squeezing the fingerpads 26 together to radially deform the housing 12. The direction of movement of the carrier 50 in the housing 12 is identified by arrow 94 in FIG. 8. In the puncturing position or configuration shown in FIG. 8, the skin puncturing element 52 of the skin puncturing assembly 14 reaches its maximum extension from the distal end 16 of the housing 12 and is driven under the force of the drive spring 70 into the skin of the patient (not shown). The drive spring 70 preferably has sufficient stored energy to cause the sharp distal tip 54 of the skin puncturing element 52 to pierce the skin of a person or animal once the carrier 50 is released from internal engagement with the housing 12.

Figure 9:
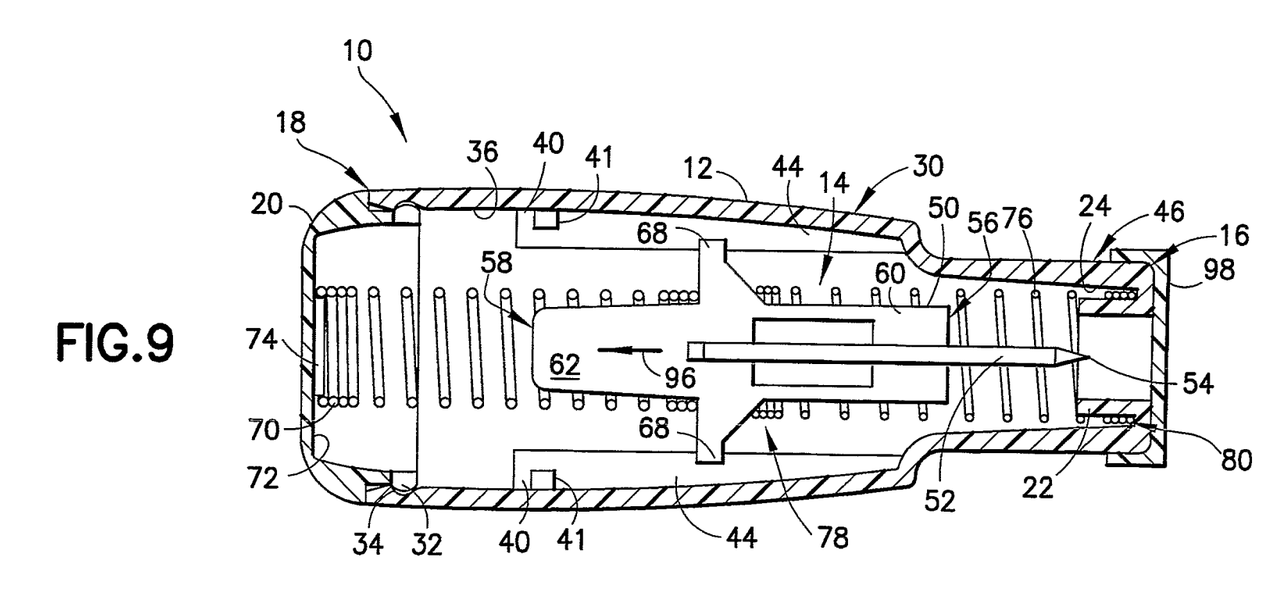
FIG. 9 is a cross-sectional view of the medical puncturing device shown in FIGS. 1 and 2, showing the device after actuation with the skin piercing element returned into the body of the device.

FIG. 9 shows the ultimate disposition of the carrier 50 within the housing 12 after the puncturing device 10 has been activated. As the carrier 50 reaches the puncturing position wherein the sharp distal tip 54 of the skin puncturing element 52 is fully exposed, the retraction spring 76 is compressed between the distal portion 60 of the carrier 50 and the distal end 16 of the housing 12, as shown in FIG. 8. The compression of the retraction spring 76 provides a return or retraction force that acts on the carrier 50 to move the carrier 50 in a return or retraction direction in the housing 12 as identified with arrow 96 in FIG. 9, which returns or retracts the skin puncturing element 52 and the sharp distal tip 54 thereof fully into the housing 12. The retraction spring 76 thereafter prevents the re-emergence of the skin puncturing element 52 from the housing 12. If desired, a distal end cap 98 may be provided to enclose the distal end 16 of the housing 12 to further ensure that the skin puncturing element 52 will not extend outward from the housing 12 after the puncturing device 10 has been activated. The retraction spring 76 may be eliminated in the puncturing device 10 and the drive spring 70 used alone in the puncturing device 10. In this embodiment, tension force in the drive spring 70 is preferably sufficient to return the carrier 50 to the retracted position or configuration shown in FIG. 9. The variation of the puncturing device 10 having reversed locations for the detents 66 and internal pockets 40 operates in substantially the same manner to the procedure described hereinabove.

Figures 11, 12:
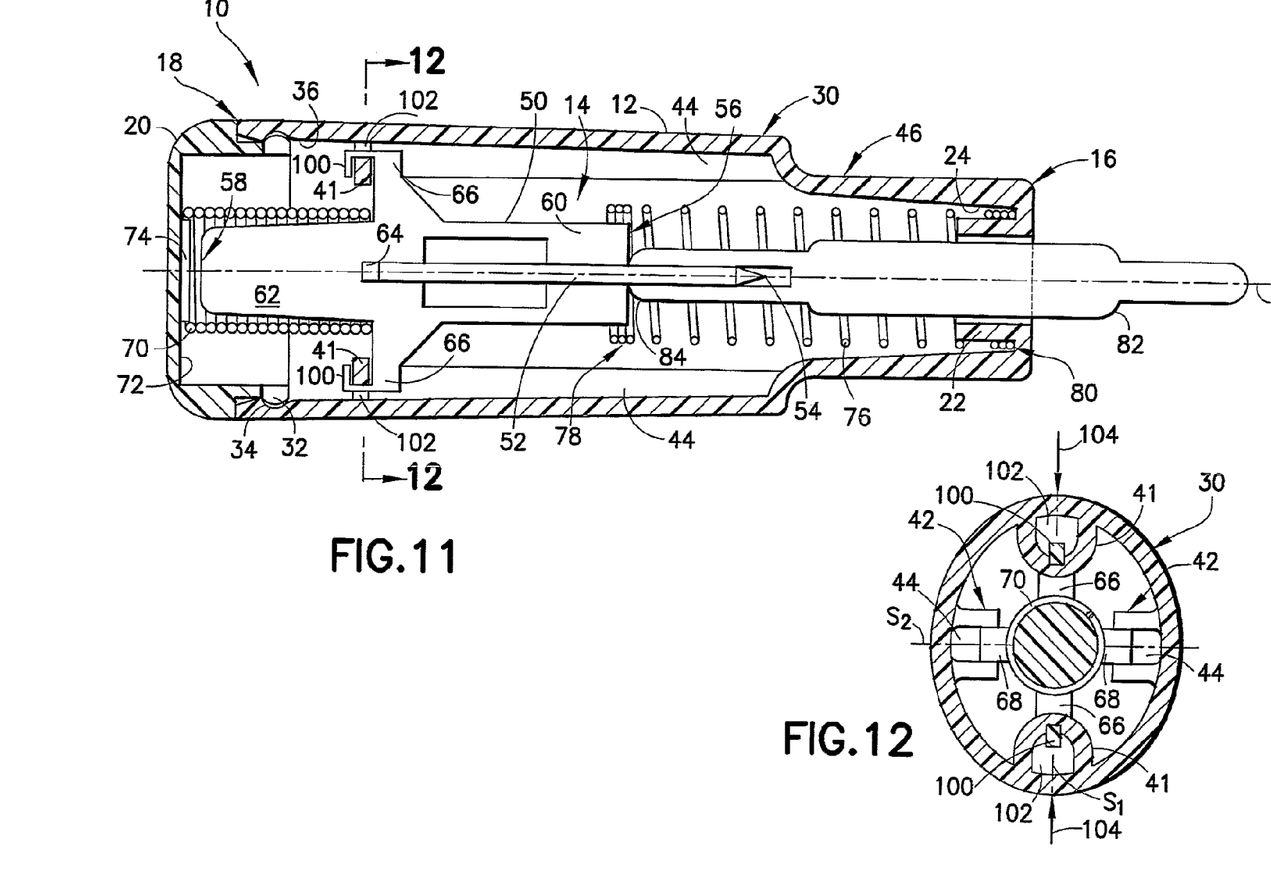
FIG. 11 is a cross-sectional view of an alternative embodiment of the medical puncturing device of the present invention.
FIG. 12 is a cross-sectional view taken along line 12-12 in FIG. 11, showing the direction of forces applied to actuate the device.

FIGS. 11 and 12 show an alternative embodiment of the puncturing device 10, which is substantially similar in structure to the puncturing device 10 shown in FIGS. 1-9. The alternative embodiment of the puncturing device 10 generally modifies the interfering detent structure provided between the carrier 50 and the housing 12 described previously. In particular, the detents 66 on the carrier 50 are now preferably formed with respective hook elements or engagement members 100. The hook elements or engagement members 100 are preferably formed integrally with the detents 66 and the body of the carrier 50. The opposing internally-extending portions 41 of the housing 12 define hook-receiving openings 102 for receiving the hook elements or engagement members 100. The hook elements or engagement members 100 are generally adapted to engage the internally-extending portions 41 to maintain the carrier 50 in the retracted position within the housing 12. In operation, to allow the carrier 50 to move from the retracted position to the extended or puncturing position, the user of the puncturing device 10 will apply inward radial pressure on the housing 12 along axis $S_1$ (i.e., the long radius of the housing 12), as represented by arrows 104 in FIG. 12. For this purpose, the fingerpads 26 may be oriented substantially along axis $S_1$ rather than axis $S_2$. As radial pressure is applied, the housing 12 will deform along axis $S_2$ (i.e., the short radius of the housing 12) by expanding along axis $S_2$. As the housing 12 deforms along axis $S_2$, the hook elements or engagement members 100 disengage from the internally-extending portions 41 of the housing 12, thereby releasing the carrier 50 to move distally in the housing 12 to the extended or puncturing position. As will be appreciated, the locations of the hook elements or engagement members 100 and hook-receiving openings 102 may be reversed in accordance with the present invention. Thus, the detents 66 may define the hook-receiving openings 102 and the internally-extending portions 41 of the housing 12 may be formed with the hook elements or engagement members 100. The puncturing device 10 will operate in an identical manner as that described hereinabove with such a reversal, which is within the skill of those skilled in the art.

While the present invention was described with reference to preferred embodiments of the medical puncturing device, those skilled in the art may make modifications and alterations to the present invention without departing from the scope and spirit of the invention. Accordingly, the above detailed description is intended to be illustrative rather than restrictive. The invention is defined by the appended claims, and all changes to the invention that fall within the meaning and range of equivalency of the claims are to be embraced within their scope.

What is claimed is:
1. A medical puncturing device, comprising:
a deformable housing, wherein at least a portion of the deformable housing includes a cross-section being continuous in a circumferential direction and perpendicular to a longitudinal axis of the housing, wherein a portion of the cross-section includes at least one point of deformation; and a skin puncturing element disposed within the housing, and maintained in a retracted first position within the deformable housing wherein a tip of the skin puncturing element is disposed within the deformable housing, the skin puncturing element being maintained in the first position against a biasing force prior to deformation of the deformable housing through an interference engagement between the deformable housing and the skin puncturing element, wherein, upon deformation of the housing at the at least one point of deformation, the skin puncturing element is movable from the first position to a second position causing the tip to be exposed.

2. The medical puncturing device of claim 1, further comprising:

a carrier configured to move within the housing, wherein the skin puncturing element is mounted to the carrier and moves in concert with the carrier.

3. The medical puncturing device of claim 2, further comprising at least one guide within the housing for guiding the movement of the skin puncturing element from the first position to the second position.

4. The medical puncturing device of claim 3, wherein the at least one guide comprises:

at least one guide element provided on one of the housing and carrier; and at least one guide track cooperating with the at least one guide element and formed in the other of the housing and carrier for guiding the movement of the carrier from the first position to the second position.

5. The medical puncturing device of claim 2, further comprising:

at least one detent provided on one of the housing and carrier; and at least one engagement formed in the other of the housing and carrier cooperating with said at least one detent, wherein the at least one engagement secures the carrier in the first position until deformation of the housing.

6. The medical puncturing device of claim 2, further comprising a drive spring disposed within the housing and acting between the carrier and a proximal end of the housing, the drive spring adapted to move the carrier from the first position to the second position upon deformation of the housing.

7. The medical puncturing device of claim 6, wherein the drive spring is integral with at least one of the housing and the carrier.

8. The medical puncturing device of claim 2, further comprising a retraction spring disposed within the housing and acting between the carrier and the distal end of the housing, the retraction spring adapted to return the carrier to a position within the housing wherein the housing encompasses the skin puncturing element after the carrier reaches the second position.

9. The medical puncturing device of claim 2, wherein an external surface of the housing comprises opposing finger pads for grasping by a user of the device and applying radial force to the housing to deform the housing.

10. The medical puncturing device of claim 2, wherein the housing comprises opposing external finger pads for applying radial force to deform the housing, and wherein the carrier comprises at least one detent cooperating with at least one engagement in the housing for securing the carrier in the first position until deformation of the housing, the opposing finger pads located along an axis oriented approximately perpendicular to an axis passing substantially through the at least one engagement to release the at least one detent from the at least one engagement upon deformation of the housing.

11. The medical puncturing device of claim 1, wherein the cross-section is defined by a plane perpendicular within 20° from a longitudinal axis through the puncturing device.

12. A medical puncturing device, comprising:

a deformable housing having a proximal end and a distal end, wherein at least a portion of the deformable housing includes a cross-section being continuous in a circumferential direction and perpendicular to a longitudinal axis of the housing, wherein a portion of the cross-section includes at least one point of deformation;

a skin puncturing assembly disposed within the housing and comprising a movable carrier and a skin puncturing element mounted to the carrier, the skin puncturing element comprising a distal tip for puncturing the skin of a patient, the carrier movable from a retracted position wherein the sharp distal tip is disposed within the housing to a puncturing position wherein the distal tip is exposed to puncture the skin of the patient, the carrier being maintained in the retracted position against a biasing force prior to deformation of the deformable housing;

wherein one of the housing and carrier includes at least one detent in interference engagement with at least one engagement formed in the other of the housing and carrier for securing the carrier in the retracted position against the biasing force; and wherein radial deformation of the housing causes the at least one detent to move out of interference engagement with the at least one engagement, such that the carrier is moved from the retracted position to the puncturing position.

13. The medical puncturing device of claim 12, further comprising at least one internal guide for guiding the movement of the carrier from the retracted position to the puncturing position.

14. The medical puncturing device of claim 13, wherein the at least one internal guide comprises at least one guide element provided on one of the housing and carrier and cooperating with the at least one guide track formed in the other of the housing and carrier for guiding the movement of the carrier from the retracted position to the puncturing position.

15. The medical puncturing device of claim 12, further comprising a drive spring disposed within the housing and acting between the carrier and the proximal end of the housing, the drive spring adapted to move the carrier from the retracted position to the puncturing position upon deformation of the housing.

16. The medical puncturing device of claim 15, further comprising a spring disposed within the housing and acting between the carrier and the distal end of the housing, the spring adapted to return the carrier to a position within the housing wherein the housing encompasses the skin puncturing element after the carrier reaches the puncturing position.

17. The medical puncturing device of claim 12, further comprising a drive spring disposed within the housing and acting between the carrier and the proximal end of the housing, the drive spring adapted to move the carrier from the retracted position to the puncturing position upon deformation of the housing and having sufficient tension force to return the carrier to a position within the housing wherein the housing encompasses the skin puncturing element after the carrier reaches the puncturing position.

18. The medical puncturing device of claim 12, wherein an external surface of the housing comprises opposing finger pads for applying radial force to deform the housing, the opposing finger pads located along an axis oriented approximately perpendicular to an axis passing substantially through the at least one internal pocket upon deformation of the housing.

19. The medical puncturing device of claim 12, wherein the skin puncturing element comprises a needle or a blade.

20. The medical puncturing device of claim 12, wherein the at least one engagement comprises an internal pocket.

21. A medical puncturing device, comprising:
 a deformable housing, wherein at least a portion of the deformable housing includes a cross-section being continuous in a circumferential direction and perpendicular to a longitudinal axis of the housing, wherein a portion of the cross-section includes at least one point of deformation; and
 a skin puncturing element disposed within the housing and maintained in a retracted first position within the deformable housing wherein a tip of the skin puncturing element is disposed within the deformable housing, the skin puncturing element being maintained in the first position against a biasing force prior to deformation of the deformable housing through an interference engagement between the deformable housing and the skin puncturing element,
 wherein, upon radial deformation of the housing, the skin puncturing element is movable from the first position to a second position causing the tip to be exposed.

22. The medical puncturing device of claim 21, further comprising:
 a carrier configured to move within the housing, wherein the skin puncturing element is mounted to the carrier and moves in concert with the carrier.

23. The medical puncturing device of claim 22, further comprising at least one guide within the housing for guiding the movement of the skin puncturing element from the first position to the second position.

24. The medical puncturing device of claim 22, further comprising:
 at least one detent provided on one of the housing and carrier; and
 at least one engagement formed in the other of the housing and carrier cooperating with said at least one detent,
 wherein the at least one engagement secures the carrier in the first position until deformation of the housing.

25. The medical puncturing device of claim 21, wherein an external surface of the housing comprises opposing finger pads for grasping by a user of the device and applying radial force to the housing to deform the housing.

* * * * *

UNITED STATES PATENT AND TRADEMARK OFFICE
CERTIFICATE OF CORRECTION

PATENT NO. : 8,449,479 B2  
APPLICATION NO. : 11/568603  
DATED : May 28, 2013  
INVENTOR(S) : Radzuinas et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1745 days.

Signed and Sealed this
Eighth Day of September, 2015

Michelle K. Lee
*Director of the United States Patent and Trademark Office*